United States Patent [19]
Rider

[11] Patent Number: 6,087,114
[45] Date of Patent: Jul. 11, 2000

[54] OPTOELECTRONIC SENSOR

[75] Inventor: Todd H. Rider, Acton, Mass.

[73] Assignee: Massachusetts Institute of Technology, Cambridge, Mass.

[21] Appl. No.: 08/987,410

[22] Filed: Dec. 9, 1997

[51] Int. Cl.[7] ...................... G01N 33/543; G01N 33/554
[52] U.S. Cl. ............................ 435/7.2; 385/12; 385/129; 422/55; 422/58; 422/82.05; 422/82.06; 422/82.07; 422/82.08; 422/82.09; 422/82.11; 435/7.21; 435/287.1; 435/287.2; 435/288.7; 435/808; 436/164; 436/172; 436/518; 436/527; 436/536; 436/805; 436/519
[58] Field of Search ........................ 385/12, 129; 422/55, 422/58, 82.05, 82.06, 82.07, 82.08, 82.09, 82.11; 435/7.2, 7.21, 287.1, 287.2, 288.7, 808; 436/164, 172, 518, 527, 536, 805, 519

[56] References Cited

U.S. PATENT DOCUMENTS

| | | | |
|---|---|---|---|
| 5,126,276 | 6/1992 | Fish et al. ................................ | 436/531 |
| 5,139,937 | 8/1992 | Inouye et al. ........................... | 435/69.1 |
| 5,360,728 | 11/1994 | Prasher .................................... | 435/189 |
| 5,541,309 | 7/1996 | Prasher .................................... | 536/23.2 |
| 5,714,666 | 2/1998 | Pritchett et al. ............................ | 800/2 |
| 5,798,441 | 8/1998 | Cormier et al. ......................... | 530/324 |

OTHER PUBLICATIONS

Button et al., "Aequorin–expressing Mammalian Cell Lines Used to Report $Ca^{2+}$ Mobilization", Cell Calcium 14:663–671, 1993.
Chalfie, "Green Fluorescent Protein", Photochemistry and Photobiology 62:651–656, 1995.
Mosier, "Primary In Vitro Antibody Responses by Purified Murine B Lymphocytes in Serum–Free Defined Medium", The Journal of Immunology 127:1490–1493, 1981.
Paddle, "Biosensors for Chemical and Biological Agents of Defence Interest", Biosensors & Bioelectronics 11:1079–1113, 1996.
Page et al., "A Cell–based Immunobiosensor with Engineered Molecular Recognition—Part II: Enzyme Amplification Systems", Biosensors & Bioelectronics 12:457–466, 1997.
Pizziconi et al., "A Cell–based Immunobiosensor with Engineered Molecular Recognition—Part I: Design Feasibility", Biosensors & Bioelectronics 12:287–299, 1997.
Shimomura et al., "Calcium Binding, Quantum Yield, and Emitting Molecule in Aequorin Bioluminescence", Nature 227:1356–1357, 1970.
Shimomura et al., "Light–emitting Properties of Recombinant Semi–Synthetic Aequorins and Recombinant Fluorescein–conjugated Aequorin for Measuring Cellular Calcium", Cell Calcium 14:373–378, 1993.
Wilson et al., "Crosslinkage of B Lymphocyte Surface Immunoglobulin by Anti Ig or Antigen Induces Prolonged Oscillation of Intracellular Ionized Calcium", Journal of Experimental Medicine 166:601–606, 1987.
Wilson et al., "The B Lymphocyte Calcium Response to Anti–Ig Is Dimished by Membrane Immunoglobulin Cross–Linkage . . . ", The Journal of Immunology 138:1712–1718, 1987.

*Primary Examiner*—Christopher L. Chin
*Attorney, Agent, or Firm*—Fish & Richardson P.C.

[57] ABSTRACT

A device for detecting the presence of an antigen including (1) a cell having antibodies which are expressed on the surface of the cell and are specific for the antigen to be detected, where binding of the antigen to the antibodies results in an increase in calcium concentration in the cytosol of the cell, the cell further having a emitter molecule which, in response to the increased calcium concentration in the cytosol, emits a photon; (2) a liquid medium for receiving the antigen and in which the cell is immersed; and (3) an optical detector arranged for receiving the photon emitted from the cell.

10 Claims, 2 Drawing Sheets

OPTOELECTRONIC SENSOR

This invention was made with government support under Contract number F19628-95-C-0002 awarded by the Air Force. The government has certain rights in the invention.

BACKGROUND OF THE INVENTION

The need for small, fast, and sensitive detectors of biological agents which are able to continuously monitor an environment for extended periods of time is underscored by the proliferation of biological and chemical weapons, the poor man's nuclear weapon. Under battlefield conditions, a useful detector would rapidly alert a soldier when a specific biological or chemical agent is detected so that countermeasures can quickly be implemented.

Such detectors would be useful in non-military applications as well. Rapid detection of antibiotic-resistant bacteria in a patient would help clinicians select a more effective therapeutic regimen. Continuous monitoring of a city's drinking water supply would provide early warning of potential pathogens, giving public works officials more time to manage the potential health risks to the public. In addition, the use of these detectors in meat and poultry inspections would be a significant improvement over the current "poke-and-smell" procedure.

All vertebrates acquire a specific immune response to a foreign agent (antigen) in part by generating an immense diversity of antibody molecules. Antibody molecules bind to antigen with high specificity, e.g., they can differentially bind to two closely related strains of bacteria or viruses.

Antibodies are produced by B cells, a crucial component of the immune system. An antigen can activate a B cell by binding to antibodies on its surface, leading to a cascade of intracellular biochemical reactions which causes a calcium ion influx into the cytosol of the B cell.

For a review of antibody structure and function and B cell activation, see Paul, editor, *Fundamental Immunology*, 3rd ed., Raven Press, New York (1993).

SUMMARY OF THE INVENTION

This invention relates to a device for detecting an antigen. The device includes a liquid medium containing cells and an optical detector, the liquid medium receiving the antigen. Each of the cells has antibodies which are expressed on its surface and are specific for the antigen to be detected. Binding of the antigen to the antibodies results in an increase in calcium concentration. The cells also contain emitter molecules (e.g., aequorin) in their cytosol which emit photons in response to the increased calcium concentration in the cytosol. The detector can be separated from the medium containing the cells by a covering (e.g., glass) that is transparent to the photons. Such a covering can serve to support the medium, protect a fragile surface of the detector, or be used as a lens. The optical detector, e.g., a charge-coupled device (CCD) is able to detect the photons emitted from the cells in response to the increased calcium concentration and indicate to the user that the antigen to be detected is present. Other optical detectors which can be used in the device include a photomultiplier tube or a photodiode. Preferably, the optical detector is able to distinguish individual cells.

The device can be contained within a housing made from, for example, aluminum, plastic, or stainless steel. Such a housing can prevent contamination of the device with extraneous organisms. The housing preferably includes two halves attached to each other on one side of the housing by a hinge joint. In applications where an airborne antigen is to be detected, the housing can contain one or more openings for the antigen to pass into the device. Such an opening is preferably screened by an antigen-permeable barrier such as a metal mesh or a membrane.

The sample containing the antigen can pass through a filter before the antigen contacts the cells. Suitable filters include passive filters (e.g., filter with determined pore sizes, affinity columns or immunofilters) and active filters (e.g., fluorescence-activated sorters, active size sorters, or microfluidic systems).

The invention also features a method for detecting the presence of an antigen, which includes providing a sample (e.g., a volume of air) suspected of containing the antigen; introducing the sample into a device containing cells immersed in a medium; and monitoring photon emission as an indication of whether the antigen is present. The cells used in this method are described above.

Other features or advantages of the present invention will be apparent from the following drawings, detailed description, and the claims. Any publications cited in this disclosure are hereby incorporated by reference.

DETAILED DESCRIPTION OF THE INVENTION

Figure 1:
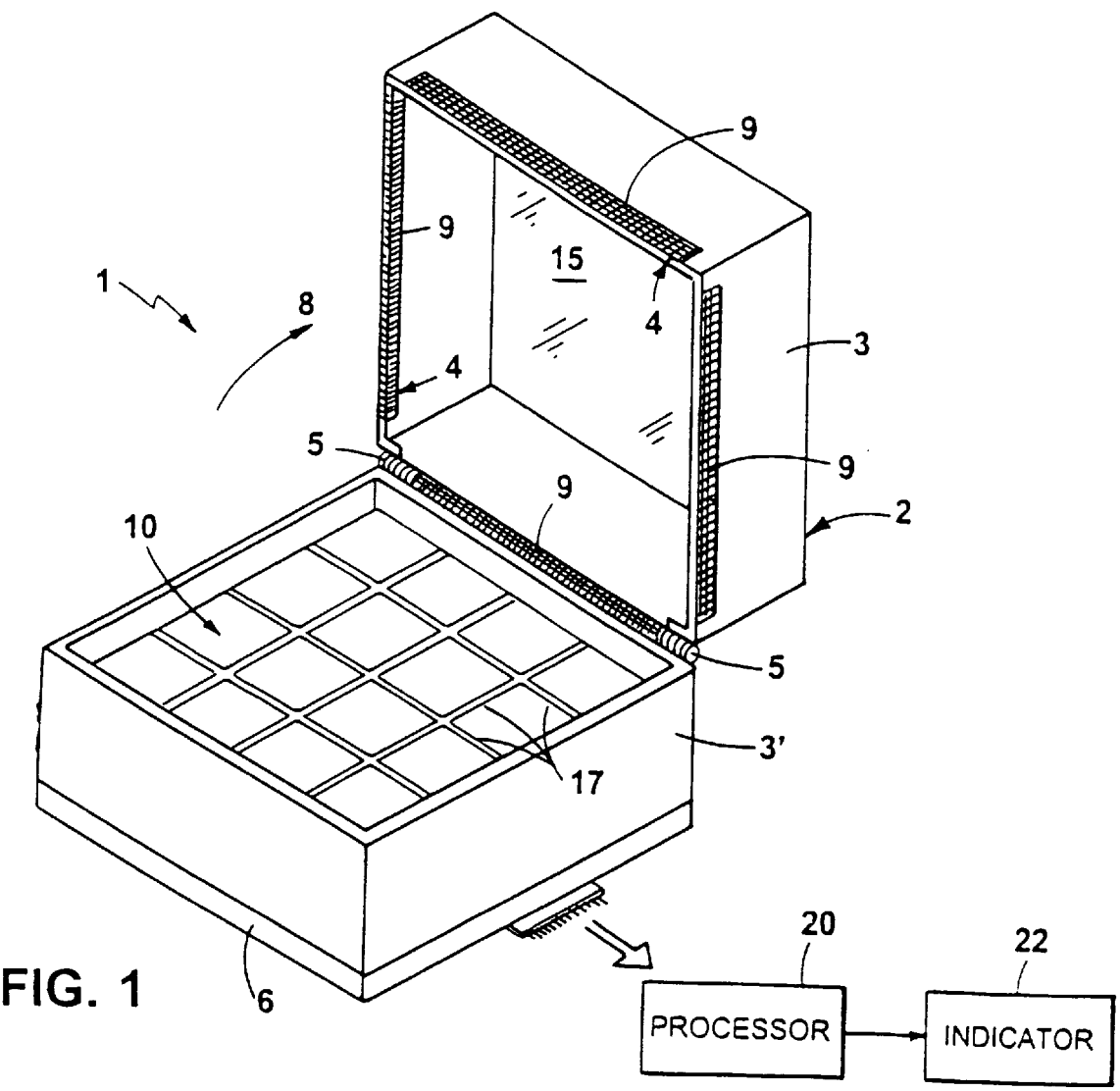
FIG. 1 is perspective view of a device for detecting an antigen in its open position.
Figure 2:
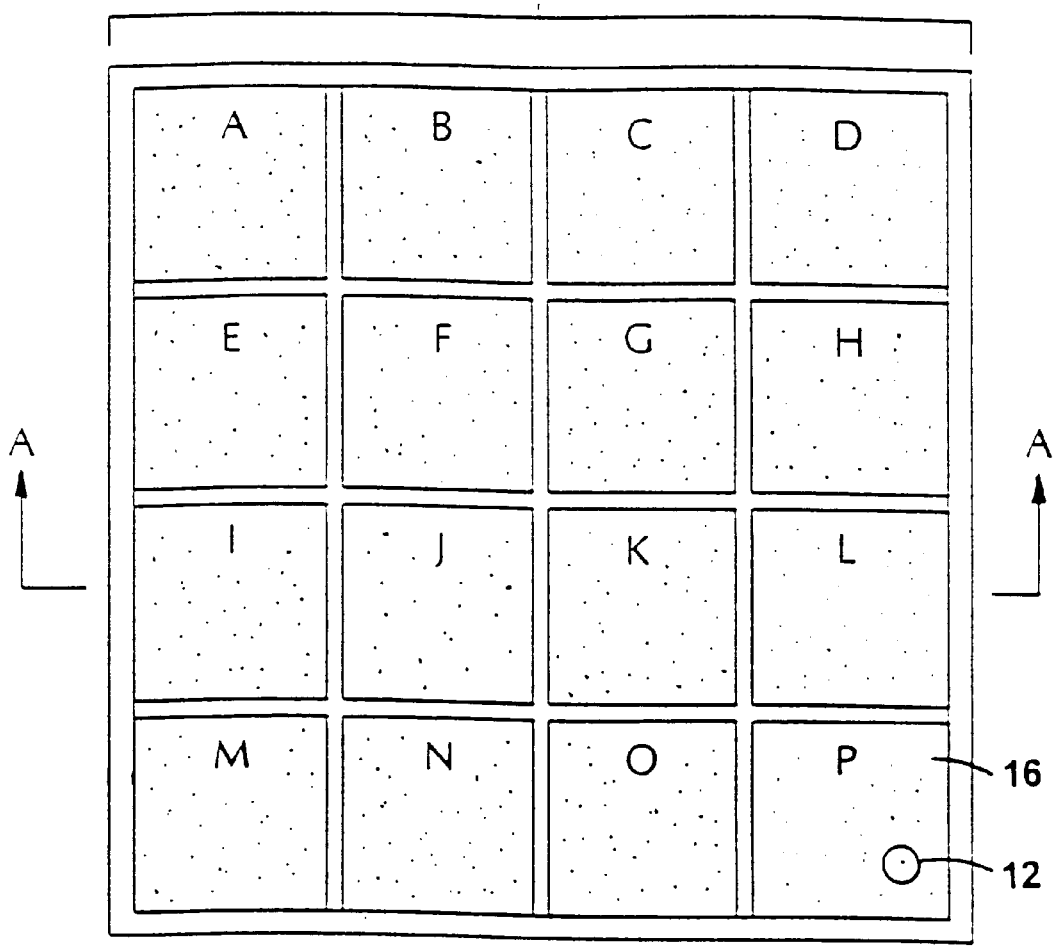
FIG. 2 is a top view of the device in FIG. 1 with the upper half of the housing removed.
Figure 3:
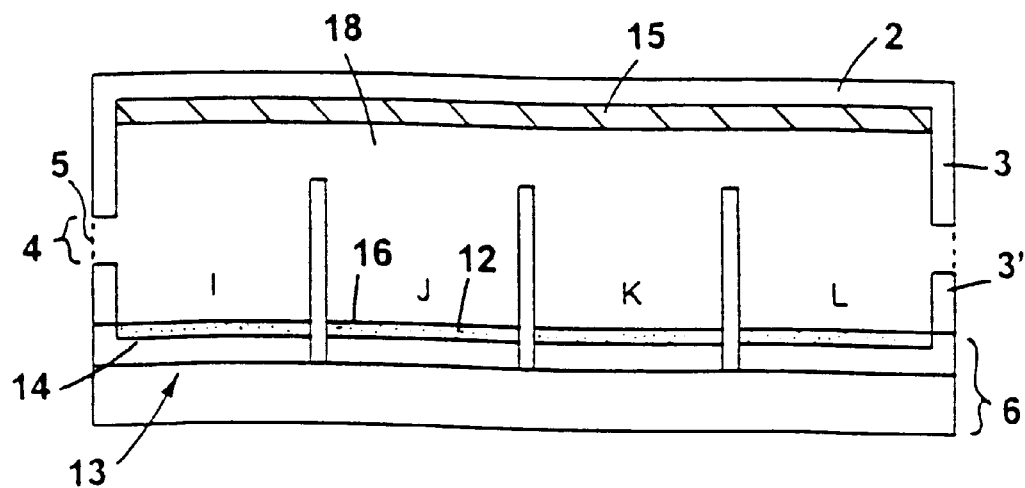
FIG. 3. is a cross-sectional view of the device taken along sectional line A—A of FIG. 2.

Referring to FIGS. 1–3, a device 1 for detecting multiple airborne antigens includes a housing 2 having an upper half 3 and a lower half 3' which together define an inner volume 18 (FIG. 3) of the device. When upper half 3 and lower half 3' are together (closed position), they also define an opening 4 through which the antigen to be detected enters the device 2. An antigen-permeable mesh 9 is positioned over the opening 4 to prevent the ingress of large particles which could interfere with proper functioning of the inner components. The upper half 3 of the housing 1 is attached to the lower half 3' by hinge 5, allowing the device 1 to be opened in a direction as indicated by arrow 8. Lower half 3' has an open bottom to receive an optical detector, here a CCD 6, which is discussed in greater detail below.

The top view of the device 1 when the upper half 3 of the housing 2 is removed is shown in FIG. 2. The device 1 includes an array 10 of sectors A–P, each sector includes liquid medium 16 containing cells 12 immersed therein. The liquid media 16 in the sectors are separated from each other by walls 17 to prevent intermixing of cells in each sector. The specific cells provided within the medium of a sector can all be the same type or may be specific to a particular antigen to be detected. In the latter case, the device 2 is capable of detecting a variety of different antigens. Although walls 17 are used as barriers in this embodiment, they are not always necessary. For instance, when the medium containing the cells are droplets of an aqueous solution, the droplets remain within the sector by water surface tension. Alternatively, the barriers can be edged grooves running between the sectors, in which case water surface tension at the edge of the groove will keep the droplets from intermixing. In another example, the cells are adhered to a surface and intermixing of the media in different sectors is not a problem.

Referring to FIG. 3, the optical detector 6 includes a detection surface 13. The optical detector has a glass covering 14 which is in contact with the liquid medium 16 containing cells 12. To increase photon detection efficiency, the device 1 includes a photon reflective layer 15 located on the inner surface of upper half 3 of the housing 2.

When the antigen to be detected binds to the antibodies on the surface of cells 12, calcium ions move into the cytosol as described in Wilson et al., J Exp Med 166:601–606 (1987). The increased cytosolic calcium concentration causes an emitter molecule to emit a photon, which is read by the optical detector 6. In a preferred embodiment, each cell will have multiple copies of the emitter molecule and will emit multiple photons when activated. Optical detector 6 provides electrical signals representative of an image of array 10. The electrical signals are processed to indicate which of sectors of array 10 have detected the presence of an antigen. For example, the signals are received by a processor 20 which is connected to indicator 22 (e.g., a light or sound emitting device) of the presence of one or more of the antigens. In one embodiment, for example, indicator 22 includes lamps, each of which is associated with one of the sectors of array 10 and provides an indication of the presence of the antigen associated with that sector.

The arrangement of the optical detector 6 with respect to the media containing the cells can be varied. For example, the medium 16 could fill inner volume 18 between the glass covering 14 and the reflective layer 15, and the opening 4 is covered by a membrane or porous filter instead of mesh 9. In this case, the cells adhere to glass covering 14, rendering any walls 17 between sectors unnecessary. To facilitate adherence of the cells 12 to the glass covering 14, the glass can be coated with substances (e.g., poly-L-lysine or extracellular matrix proteins). In this variation of the device, an antigen in a liquid can be detected as long as the liquid containing the antigen contacts the membrane and diffuses through medium 16 to the cells 12. Alternatively, the housing 2 can be opened by pivoting upper half 3 and a liquid sample containing the antigen to be detected can be dropped into the medium 16.

The liquid medium 16 can contain nutrients, dissolved gases, cytokines, antibiotics (to inhibit contamination), or any other substance necessary for maintenance of the cells. Furthermore, the liquid medium can contain substances to aid the detection of calcium in activated cells (e.g., coelenterazine substrate or analogues thereof to recharge spent aequorin molecules or calcium-sensitive fluorescent substances). If necessary, the medium is maintained at a suitable temperature or pH.

The cell which has surface-bound antibodies can be either prokaryotic or eukaryotic. Upon binding of antigen to the antibodies, the cell mobilizes calcium ions into the cytosol. A preferred cell is a B cell (more preferably, a B cell from a poikilothermic animal) which can be genetically engineered to express a surface-bound monoclonal antibody, or it can be produced by, for example, immunizing an animal with the antigen to be detected and harvesting the B-cell from the immunized animal. In addition, growth of the cell can be controlled by any means well known in the art, including providing anti-mitotic drugs (e.g., α-amanitin) or growth factors (e.g., fetal bovine serum) in the medium. Alternatively, cells can be genetically engineered to grow at a determined rate. Any cell suitable can be used as long as binding of the antigen to the antibodies on the surface of the cell leads to an increase in calcium concentration in the cytosol. In fact, the cell can be a non-living, manufactured unit as long as it satisfies the above requirement.

A suitable emitter molecule is any molecule that will emit a photon in response to elevated cytosolic calcium concentrations, including bioluminescent and fluorescent molecules. One preferred emitter molecule, the bioluminescent aequorin protein, is described in Button et al., Cell Calcium 14:663–671 (1993); Shimomura et al., Cell Calcium 14:373–378 (1993); and Shimomura, Nature 227:1356–1357 (1970). Aequorin generates photons by oxidizing coelenterazine, a small chemical molecule. Coelenterazine diffuses through cellular membranes, so coelenterazine or an analog thereof can be added to the culture medium surrounding the cells. Alternatively, genes encoding enzymes that make coelenterazine can be introduced into the cells. In another embodiment, bioluminescent green fluorescent protein (GFP) can be used (see Chalfie, Photochem Photobiol 62:651–656 [1995]). In this embodiment, the cell cytosol contains both GFP and aequorin. In response to elevated calcium in the cytosol, aequorin donates energy to GFP in an emissionless energy transfer process. GFP then emits the photon. Alternatively, the emitter molecule can be a calcium-sensitive fluorescent molecule (e.g., indo-1) which is illuminated with a light source emitting a wavelength of light suitable to induce fluorescence.

Aequorin, or any other emitter molecule, can be introduced into the cell by methods well know in the art. If the emitter molecule is a protein (as is the case with aequorin), the cell can contain an expression vector encoding the protein (i.e., a nucleic acid or virus which will produce the emitter molecule when introduced into a cell). An expression vector can exist extrachromosomally or integrated into the cell genome.

The antigen can be introduced into the device passively. For example, airborne anthrax bacteria can enter the device through an opening via air currents. Alternatively, an airborne antigen can be actively introduced into the device, e.g., by a fan. The antigen to be detected can also reside in an aqueous medium. For example, a drop of the aqueous sample can be added to the medium containing the cells.

Instead of grouping cells in sectors within an array, the cells specific for different antigens can be interspersed if the photon emitted from a cell specific for one antigen is of a wavelength different from the photon emitted from a cell specific for another antigen. In such a situation, the optical detector can differentially detect the photons of different wavelengths. For example, Cells sensitive to different antigens can contain different aequorin-like proteins and/or different fluorescent proteins so that the different cells could be distinguished on the basis of differing photon emission characteristics (e.g., peak wavelength, spectral width of emission, or decay rate). To allow identification of a larger number of antigens, signal multiplexing can also be used. For example, the emission spectrum of a given type of cell could have multiple identifiable peaks. Different fusion proteins (e.g., aequorin and a fluorescent protein joined together by fusing their genes in frame) could be useful for this purpose.

In general, multivalent antigens (which contain multiple binding sites for a specific antibody) are required to cross-link surface antibodies on the cell in order to trigger calcium influx into the cytosol. However, monovalent antigens (which contain only one binding site for a specific antibody)

can also be detected by the device. Such antigens can be detected if several monovalent antigens are linked together (by noncovalent bonding, for example) as the antigens bind to the antibodies on the surface of the cell. Alternatively, the cell can be genetically engineered to expressed two or more antibodies which are specific to the same antigen but bind to different parts of the antigen, thereby allowing a single antigen to bind to at least two antibodies on the cell.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

For example, the device of the invention can further include pumps, valves, fluid reservoirs, batteries, microprocessors, waste removal systems, and/or temperature control systems.

If desired, different cells binding to different parts of the sample antigen could be used to look for different identifying features on the same pathogen. On the one hand, this could be useful in situations where false positives are a problem, since multiple identifying features can be detected before declaring a positive identification. On the other hand, it could also be useful where false negatives are a problem, since even if a pathogen lacks one characteristic feature, it could still be detected on the basis of the other identifying feature.

Analysis of multiple antigens by the device can be performed in parallel for suitably high concentrations of antigens, and the sample containing the antigens can be introduced into a chamber containing cells sensitive to different antigens. However, serial analysis might be necessary for lower concentrations of antigens. The antigen sample can first be delivered to a cell specific for one antigen, then carried on to a different cell specific for another antigen. In one embodiment, a fluid channel winds back and forth over the surface of the optical detector, presenting the sample to one antigen-specific sector of cells at a time. Flow in the channel can be slow enough or can be periodically stopped in order to allow antigen-antibody binding. Serial detection is generally slower than parallel detection, so additional components of the device can be added to speed the detection process. Prior information about the sample could be used to reduce the number of antigen-specific types of cells to which the sample must be presented in series. For example, if the sample is known to contain a viral antigen, then it would only have to be presented to virus-specific cells. Also, the earlier sectors in the series could be designated for the detection of higher priority antigens (e.g., more rapidly acting pathogens).

The device can also be designed so that the cell populations can be easily replaced if they are killed or otherwise rendered ineffective. The support to which the cell lines are attached or in which the media is contained would be made removable. Extra supports containing the cell lines could be frozen or freeze-dried and then stored. After removing old cells from a sensor and inserting a fresh cells, one could revive the device with the fresh cells.

After the sample has been examined by the cells, it would preferably be flushed away (via the use of a reservoir of fresh medium and a pump, for example) from the cells, thereby preparing the device for the next sample and helping to prevent contamination or clogging of the device.

What is claimed is:

1. A device for detecting the presence of an antigen, comprising:

a B cell having antibodies which are expressed on the surface of the B cell and are specific for the antigen to be detected, wherein binding of the antigen to the antibodies results in an increase in calcium concentration in the cytosol of the B cell, the B cell further having an emitter molecule which, in response to the increased calcium concentration, emits a photon;

a liquid medium in which the B cell is immersed, the liquid medium receiving the antigen to be detected; and an optical detector arranged for receiving the photon emitted from the cell.

2. The device of claim 1, further comprising a covering for the detector, the covering separating the liquid medium from the detector.

3. The device of claim 1, wherein the optical detector is a charge-coupled device.

4. The device of claim 1, further comprising a housing enclosing the liquid medium.

5. A device for detecting the presence of an antigen, comprising:

a B cell having antibodies which are expressed on the surface of the B cell and are specific for the antigen to be detected, wherein binding of the antigen to the antibodies results in an increase in calcium concentration in the cytosol of the B cell, the B cell further having an emitter molecule which, in response to the increased calcium concentration, emits a photon;

a liquid medium in which the B cell is immersed; and an optical detector arranged for receiving the photon emitted from the B cell, wherein the optical detector is adjacent to the liquid medium.

6. The device of claim 5, further comprising a covering positioned over the optical detector to support the liquid medium.

7. The device of claim 5, wherein the optical detector is a charge-coupled device.

8. The device of claim 5, further comprising a housing enclosing the liquid medium.

9. A method for detecting the presence of an antigen, comprising:

providing a sample suspected of containing the antigen;

introducing the sample into a device containing a cell immersed in a medium, the cell having antibodies which are expressed on its surface and are specific for the antigen to be detected, wherein binding of the antigen to the antibodies results in an increase in calcium concentration in the cytosol of the cell, and the cell further having an emitter molecule which, in response to the increased calcium concentration, emits a photon; and monitoring photon emission as an indication of whether the antigen is present.

10. The method of claim 9, wherein the sample is a volume of air.

* * * * *